US012629086B2

(12) United States Patent
Malik et al.

(10) Patent No.: US 12,629,086 B2
(45) Date of Patent: May 19, 2026

(54) METHOD FOR DETECTING BRAIN CONDITION STATE AND A PORTABLE DETECTION SYSTEM THEREOF

(71) Applicants: Shilpa Malik, Gujarat (IN); Anupam Lavania, Gujarat (IN)

(72) Inventors: Shilpa Malik, Gujarat (IN); Anupam Lavania, Gujarat (IN)

(73) Assignees: Shilpa Malik, Gujarat (IN); Anupam Lavania, Gujarat (IN)

( * ) Notice: Subject to any disclaimer, the term of this patent is extended or adjusted under 35 U.S.C. 154(b) by 633 days.

(21) Appl. No.: 18/008,128

(22) PCT Filed: Jun. 15, 2021

(86) PCT No.: PCT/IB2021/055274
§ 371 (c)(1),
(2) Date: Dec. 2, 2022

(87) PCT Pub. No.: WO2021/255644
PCT Pub. Date: Dec. 23, 2021

(65) Prior Publication Data
US 2023/0293087 A1    Sep. 21, 2023

(30) Foreign Application Priority Data

Jun. 16, 2020    (IN) .............................. 202021025371

(51) Int. Cl.
*A61B 5/00*        (2006.01)
*G01N 21/47*       (2006.01)

(52) U.S. Cl.
CPC .......... *A61B 5/4064* (2013.01); *A61B 5/7264* (2013.01); *G01N 21/4738* (2013.01);
(Continued)

(58) Field of Classification Search
CPC ................ A61B 5/4064; A61B 5/7264; A61B 2560/0223; A61B 2560/0431;
(Continued)

(56) References Cited

U.S. PATENT DOCUMENTS 8,353,059 B2    1/2013 Crampton et al.
8,396,268 B2    3/2013 Zabair et al.
(Continued)

FOREIGN PATENT DOCUMENTS

WO    WO 2013/142051    9/2013
WO    WO 2017/011746    1/2017

OTHER PUBLICATIONS

International Search Report in International App. No. PCT/IB2021/055274 dated Oct. 7, 2021 in 2 pages.

*Primary Examiner* — Devin B Henson
*Assistant Examiner* — Molly Halprin
(74) *Attorney, Agent, or Firm* — Knobbe, Martens, Olson & Bear, LLP

(57)            ABSTRACT

Present disclosure describes the method and system for detecting the brain condition state of a subject. Method comprising calibrating a power zone of the system in real-time and detecting a reflected signal for each of a plurality of transmitted input signals on scanning each of lobe locations of the subject after calibration. Thereafter, method comprising validating an array generated using the plurality of transmitted input signal and corresponding reflected signal for each of the lobe locations and generating a lobe fit value for the validated array using a curve fitting technique. Subsequently, method comprising computing logarithmic ratios corresponding to four pairs of contralateral lobe location, six pairs of ipsilateral lobe locations in left hemisphere and six pairs of ipsilateral lobe locations in right hemisphere using the lobe fit value and classifying the logarithmic ratios into one of brain condition state classes by (Continued)

comparing with pre-labelled logarithmic ratios stored in system.

17 Claims, 7 Drawing Sheets

(52) U.S. Cl.
CPC ................. *A61B 2560/0223* (2013.01); *A61B 2560/0431* (2013.01)

(58) Field of Classification Search
CPC ..... A61B 5/0042; A61B 5/031; A61B 5/0075; A61B 5/7282; A61B 2576/026; A61B 5/7275; A61B 5/40; A61B 5/4058; A61B 5/4076; A61B 8/0808; A61B 2018/00446; G01N 21/4738
USPC ....................................................... 600/544
See application file for complete search history.

(56) References Cited

U.S. PATENT DOCUMENTS

| | | | | |
|---|---|---|---|---|
| 8,781,543 | B2 | 7/2014 | Diab et al. | |
| 2009/0221919 | A1* | 9/2009 | Ben Dor .............. | A61B 5/4076 600/407 |
| 2014/0194740 | A1* | 7/2014 | Stein ...................... | A61B 8/565 600/455 |
| 2015/0065813 | A1* | 3/2015 | Wochlik ............... | A61B 5/7207 600/559 |
| 2016/0287117 | A1* | 10/2016 | Breakspear ............ | G16H 50/20 |
| 2021/0082566 | A1* | 3/2021 | Do ......................... | G06T 7/0012 |

* cited by examiner

| c | il | ir | Outcome | Haemorrhage type |
|---|----|----|---------|------------------|
| 0 | 1 | 1 | Haemorrhage | Bilateral |
| 0 | 1 | 0 | Error | - |
| 0 | 0 | 1 | Error | - |
| 0 | 0 | 0 | Not haemorrhage | - |
| 1 | 1 | 1 | Haemorrhage | Unilateral + Bilateral |
| 1 | 1 | 0 | Haemorrhage | Unilateral |
| 1 | 0 | 1 | Haemorrhage | Unilateral |
| 1 | 0 | 0 | Error/Haemorrhage | - |

Figure 2c

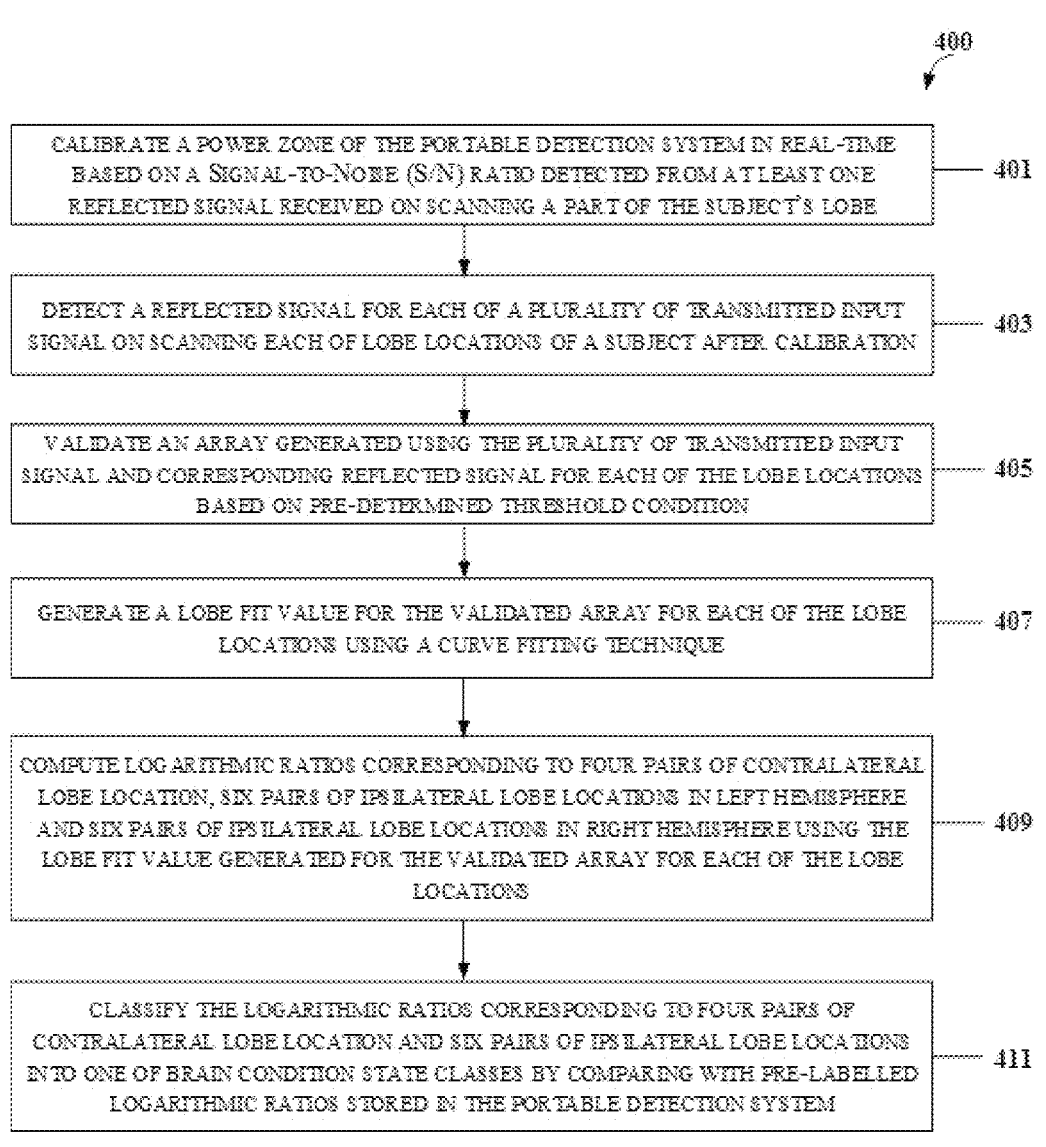

400

CALIBRATE A POWER ZONE OF THE PORTABLE DETECTION SYSTEM IN REAL-TIME BASED ON A SIGNAL-TO-NOISE (S/N) RATIO DETECTED FROM AT LEAST ONE REFLECTED SIGNAL RECEIVED ON SCANNING A PART OF THE SUBJECT'S LOBE — 401

DETECT A REFLECTED SIGNAL FOR EACH OF A PLURALITY OF TRANSMITTED INPUT SIGNAL ON SCANNING EACH OF LOBE LOCATIONS OF A SUBJECT AFTER CALIBRATION — 403

VALIDATE AN ARRAY GENERATED USING THE PLURALITY OF TRANSMITTED INPUT SIGNAL AND CORRESPONDING REFLECTED SIGNAL FOR EACH OF THE LOBE LOCATIONS BASED ON PRE-DETERMINED THRESHOLD CONDITION — 405

GENERATE A LOBE FIT VALUE FOR THE VALIDATED ARRAY FOR EACH OF THE LOBE LOCATIONS USING A CURVE FITTING TECHNIQUE — 407

COMPUTE LOGARITHMIC RATIOS CORRESPONDING TO FOUR PAIRS OF CONTRALATERAL LOBE LOCATION, SIX PAIRS OF IPSILATERAL LOBE LOCATIONS IN LEFT HEMISPHERE AND SIX PAIRS OF IPSILATERAL LOBE LOCATIONS IN RIGHT HEMISPHERE USING THE LOBE FIT VALUE GENERATED FOR THE VALIDATED ARRAY FOR EACH OF THE LOBE LOCATIONS — 409

CLASSIFY THE LOGARITHMIC RATIOS CORRESPONDING TO FOUR PAIRS OF CONTRALATERAL LOBE LOCATION AND SIX PAIRS OF IPSILATERAL LOBE LOCATIONS INTO ONE OF BRAIN CONDITION STATE CLASSES BY COMPARING WITH PRE-LABELLED LOGARITHMIC RATIOS STORED IN THE PORTABLE DETECTION SYSTEM — 411

Figure 4

METHOD FOR DETECTING BRAIN CONDITION STATE AND A PORTABLE DETECTION SYSTEM THEREOF

TECHNICAL FIELD

The present subject matter is generally related to the field of optical (screening) systems. Particularly, but not exclusively, the present disclosure relates to a method and portable detection system for detecting the brain condition state of a subject.

BACKGROUND

Point-of-care diagnosis is an important step in providing early treatment to a subject (also, referred to as a person). A fast and non-invasive screening test for brain condition state (also, referred as an intracranial bleed or brain haemorrhage) of subjects suspected with traumatic brain injury or haemorrhagic stroke at the point-of-care can result in fast triaging, which allows improved diagnostics and treatment process. But complete point-of-care testing or screening that tests brain injury remains elusive today. This is because often the subjects who sustain no external injuries or do not exhibit any clinical symptoms are missed during triage.

Regarding traumatic brain injury, one of the existing triaging methodologies is a Glasgow Coma Scale (GCS). It has proved to be an effective triaging methodology in acute traumatic brain injury cases when a subject shows clinical symptoms. However, this methodology remains inconclusive in case of mild traumatic brain injury, especially, when the subjects are asymptomatic or mildly symptomatic. This is primarily due to technology barrier(s) that prevents detection of an injury in absence of symptoms. Also, subjects wait for several hours before clinical symptoms arise, and doctors sometimes make critical decisions with incomplete information.

The existing Computed Tomography (CT) scanners are reliable diagnostic tools for brain condition state detection. However, these scanners cannot be deployed at onsite for mass screening owing to their infrastructure requirement, exposure to ionizing radiation and need of an expert radiologist to interpret the CT scan results.

The information disclosed in this background of the disclosure section is for enhancement of understanding of the general background of the invention and should not be taken as an acknowledgement or any form of suggestion that this information forms the prior art already known to a person skilled in the art.

SUMMARY

Additional features and advantages are realized through the techniques of the present disclosure. Other embodiments and aspects of the disclosure are described in detail herein and are considered a part of the claimed disclosure.

There is a huge demand for an objective assessment of the brain condition state (also, referred as an intracranial bleed or brain haemorrhage) with a portable detection system that allows paramedic or semi-skilled staff to detect brain condition state at an onsite in a fast and efficient manner.

Disclosed herein is a method for detecting the brain condition state of a subject. The method includes calibrating a power zone of the portable detection system in real-time based on a Signal-to-Noise (S/N) ratio detected from at least one reflected signal received on scanning a part of the subject's lobe. Thereafter, the method comprises detecting a reflected signal for each of a plurality of transmitted input signal on scanning each of lobe locations of the subject after calibration and validating an array generated using the plurality of transmitted input signal and corresponding reflected signal for each of the lobe locations based on predetermined threshold condition. The method comprises generating a lobe fit value for the validated array for each of the lobe locations using a curve fitting technique. Subsequently, the method comprises computing logarithmic ratios corresponding to four pairs of contralateral lobe location, six pairs of ipsilateral lobe locations in left hemisphere and six pairs of ipsilateral lobe locations in right hemisphere using the lobe fit value generated for the validated array for each of the lobe locations. Lastly, the method comprises classifying the logarithmic ratios corresponding to four pairs of contralateral lobe location and six pairs of ipsilateral lobe locations into one of brain condition state classes by comparing with pre-labelled logarithmic ratios stored in the portable detection system.

Further, the present disclosure discloses a portable detection system for detecting brain condition state of a subject. The portable detection system includes one or more processors and a memory communicatively coupled to the one or more processors, wherein the memory stores processor-executable instructions, which on execution, cause the one or more processors to calibrate a power zone of the portable detection system in real-time based on a Signal-to-Noise (S/N) ratio detected from at least one reflected signal received on scanning a part of the subject's lobe. Thereafter, the portable detection system is configured to detect a reflected signal for each of a plurality of transmitted input signal on scanning each of lobe locations of the subject after calibration and to validate an array generated using the plurality of transmitted input signal and corresponding reflected signal for each of the lobe locations based on predetermined threshold condition. The portable detection system is configured to generate a lobe fit value for the validated array for each of the lobe locations using a curve fitting technique. Subsequently, the portable detection system is configured to compute logarithmic ratios corresponding to four pairs of contralateral lobe location, six pairs of ipsilateral lobe locations in left hemisphere and six pairs of ipsilateral lobe locations in right hemisphere using the lobe fit value generated for the validated array for each of the lobe locations. Lastly, the portable detection system is configured to classify the logarithmic ratios corresponding to four pairs of contralateral lobe location and six pairs of ipsilateral lobe locations into one of brain condition state classes by comparing with pre-labelled logarithmic ratios stored in the portable detection system.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The accompanying drawings, which are incorporated in and constitute a part of this disclosure, illustrate exemplary embodiments and together with the description, serve to explain the disclosed principles. In the figures, the leftmost digit(s) of a reference number identifies the figure in which the reference number first appears. The same numbers are used throughout the figures to reference features and components. Some embodiments of system and/or methods in accordance with embodiments of the present subject matter are now described below, by way of example only, and with reference to the accompanying figures. The disclosure itself, however, as well as a preferred mode of use, further objectives, and advantages thereof, may best be understood by reference to the following detailed description of an illustrative embodiment when read in conjunction with the accompanying drawings. The novel features and characteristics of the disclosure are set forth in the appended claims.

FIG. 2c shows a table indicating specific brain condition state classes in accordance with some embodiments of the present disclosure.

FIG. 4 illustrates a flowchart showing a method for detecting the brain condition state of a subject in accordance with some embodiments of present disclosure.

Figure 1A:
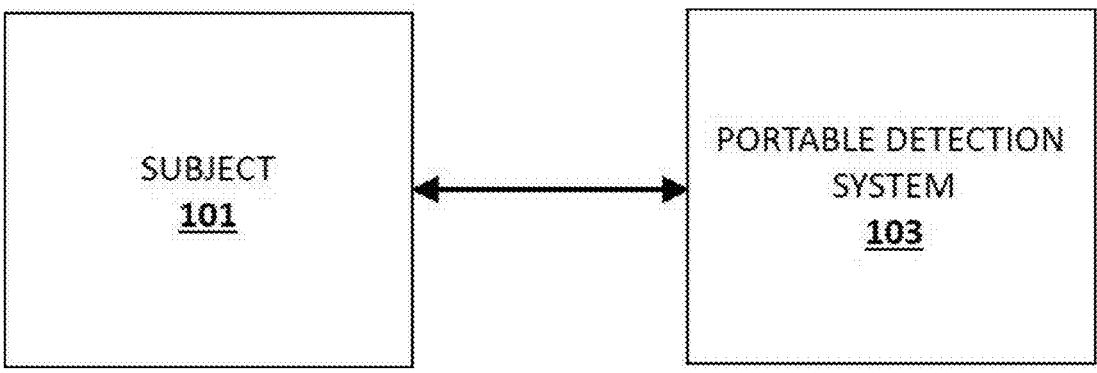
FIG. 1a illustrates an exemplary environment for detecting the brain condition state of a subject in accordance with some embodiments of the present disclosure.

It should be appreciated by those skilled in the art that any block diagrams herein represent conceptual views of illustrative systems embodying the principles of the present subject matter. Similarly, it will be appreciated that any flowcharts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however, that it is not intended to limit the disclosure to the particular forms disclosed, but on the contrary, the disclosure is to cover all modifications, equivalents, and alternatives falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus preceded by "comprises . . . a" does not, without more constraints, preclude the existence of other elements or additional elements in the system or method.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

The present disclosure discloses a method and a portable detection system for detecting the brain condition state of a subject. The method of present disclosure comprises of two parts:

(1) calibration step and (2) post-calibration steps. The calibration step involves calibrating a power zone of the portable detection system in real-time based on a Signal-to-Noise (S/N) ratio detected from at least one reflected signal received on scanning a part of the subject's lobe. This calibration step is explained in detail with reference to FIG. 2a. The post-calibration steps involve (a) detecting a reflected signal for each of a plurality of transmitted input signal on scanning each of lobe locations of the subject, (b) validating an array generated using the plurality of transmitted input signal and corresponding reflected signal for each of the lobe locations based on predetermined threshold condition, (c) generating a lobe fit value for the validated array for each of the lobe locations using a curve fitting technique, (d) computing logarithmic ratios corresponding to four pairs of contralateral lobe location, six pairs of ipsilateral lobe locations in left hemisphere (i.e., left half of the part of brain) and six pairs of ipsilateral lobe locations in right hemisphere (i.e., right half of the part of brain) using the lobe fit value generated for the validated array for each of the lobe locations and (e) classifying the logarithmic ratios corresponding to four pairs of contralateral lobe location and six pairs of ipsilateral lobe locations into one of brain condition state classes by comparing with pre-labelled logarithmic ratios stored in the portable detection system. These post-calibration steps are explained in detail with reference to FIG. 2b.

FIG. 1a illustrates an exemplary environment for detecting the brain condition state of a subject in accordance with some embodiments of the present disclosure.

Figure 1B:
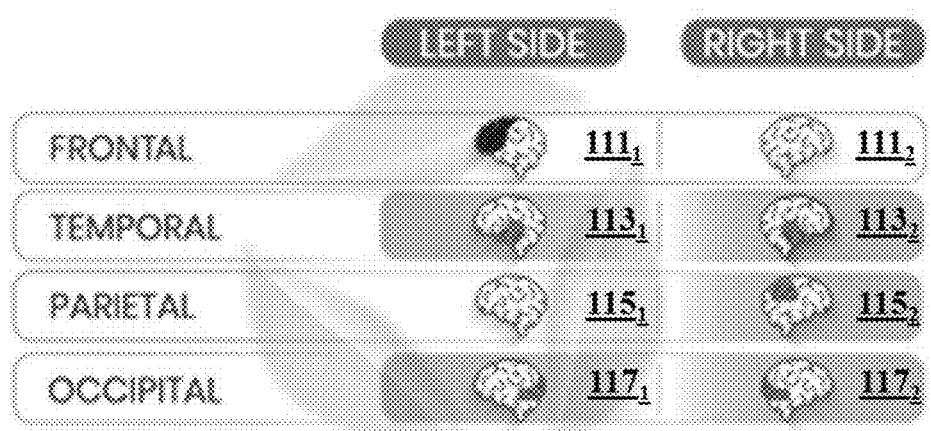
FIG. 1b illustrates lobe locations in accordance with some embodiments of the present disclosure.

As shown in FIG. 1a, the environment includes a subject 101 and a portable detection system 103. The subject 101 (also, referred to as a person) may be suspected with a brain condition state. Here, the brain condition state may refer to traumatic brain injury or brain hemorrhagic stroke or an intracranial bleed condition. The portable detection system 103 may, also, be referred to as a portable detection device. The portable detection system 103 is used to scan lobe locations of the subject 101 to detect brain condition state of the subject 101. The lobe locations may comprise of frontal left lobe $111_1$ (also, referred as frontal left side), frontal right lobe $111_2$ (also, referred as frontal right side), temporal left lobe $113_1$ (also, referred as temporal left side), temporal right lobe $113_2$ (also, referred as temporal right side), parietal left lobe $115_1$ (also, referred as parietal left side), parietal right lobe $115_2$ (also, referred as parietal right side), occipital left lobe $117_1$ (also, referred as occipital left side) and occipital right lobe $117_2$ (also, referred as occipital right side) as shown in FIG. 1b. The portable detection system 103 uses Diffuse Reflectance Spectroscopy (DRS) and linear regression analysis for detecting brain condition state of the subject 101. After calibration (to be discussed later) of the portable detection system 103, when scanning of a lobe location of the subject 101 is performed, an input signal is transmitted on to the subject's lobe location through a source probe of the portable detection system 103. In return, the portable detection system 103 detects a reflected signal through a detector probe. For each lobe location of the subject 101, a plurality of input signal and corresponding reflected signal are collected. The portable detection system 103 may include a Light-Emitting Diode (LED) to indicate the functional state of the portable detection system 103. For example, if the LED light is green, then it indicates the scanning process is in progress. The LED may be replaced/ accompanied with other types of indications like audio, haptic, etc. The portable detection system 103 may further include an LED to indicate charging state of the portable detection system 103. For example, if the LED light is green, then it indicates the battery charging process is in progress and if the LED light is red, then it indicates the battery of the portable detection system 103 needs charging. The portable detection system 103 may include a power button to switch ON or OFF the portable detection system 103 and a trigger button to start or trigger the scanning process.

The portable detection system 103 may include a display screen (also, referred to as a display) to provide a visual interface for an operator of the portable detection system 103 to view scanning results of each of the lobe locations of the subject 101. The operator may perform actions based on the commands displayed on the screen of the portable detection system 103. The display screen may provide the operator with user interface commands for placing the portable detection system 103 at defined points (i.e., lobe locations) for scanning. The display screen may, also, display error (indicating error type) if the portable detection system 103 does not perform well or if the operator mishandled the portable detection system 103 at any stage. Further, the portable detection system 103 may include a left arrow button and a right arrow button for navigating through the display screen, a home button to take the operator to home screen on the display, an Ok button to confirm input from the operator and a charging socket for charging the portable detection system 103. The portable detection system 103 may include a buzzer (i.e., sound output) to output different tones to indicate different state of the portable detection system 103 i.e., when the portable detection system 103 is powered ON, when the scanning is in progress and when an error is generated to the operator. The different tones may be a combination of different frequencies and intensities.

Figure 2A:
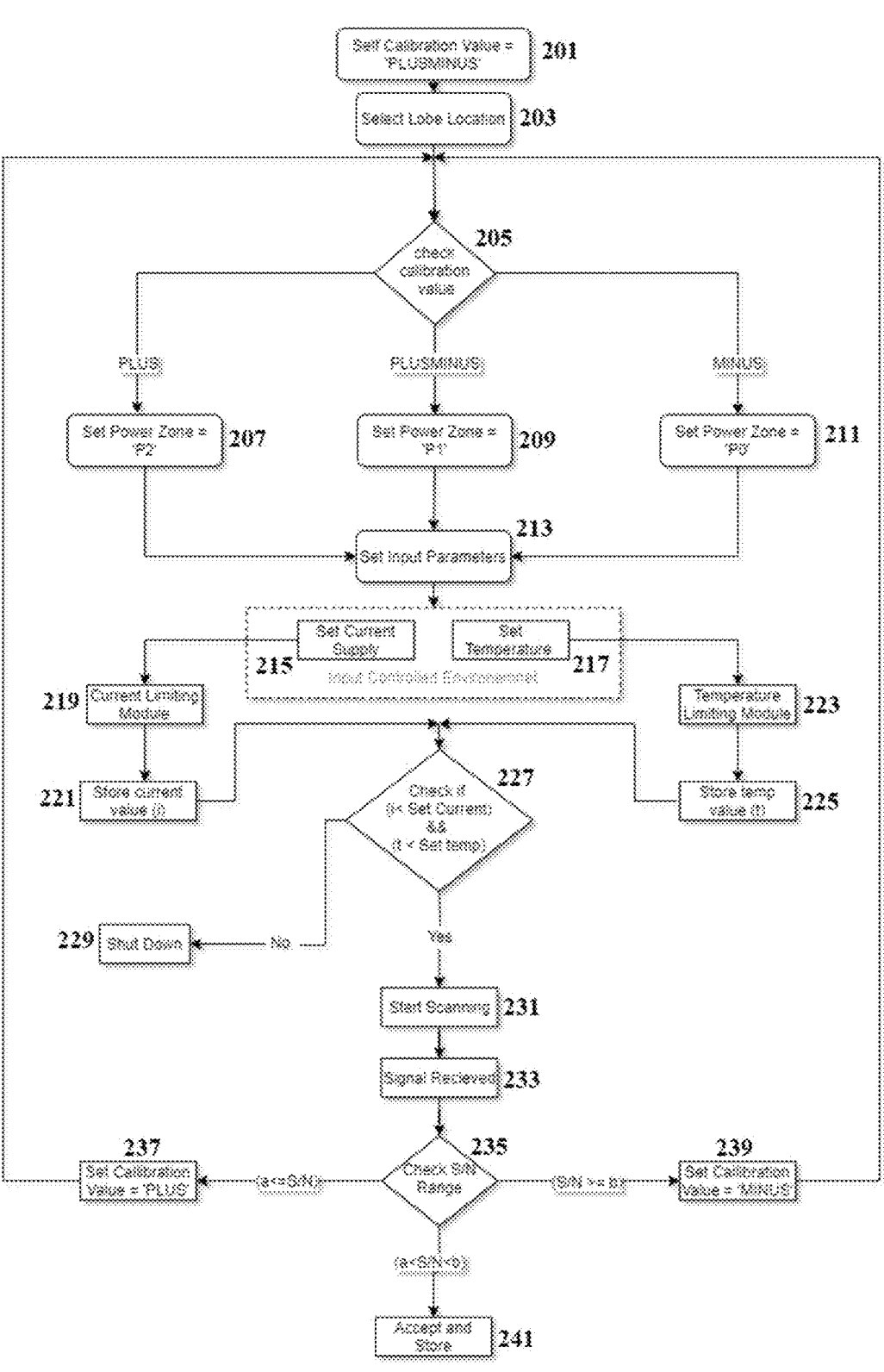
FIG. 2a illustrates a power zone calibration flow chart in accordance with some embodiments of the present disclosure.

FIG. 2a illustrates a power zone calibration flow chart in accordance with some embodiments of the present disclosure.

Prior to using the portable detection system 103 for detecting brain condition state of the subject 101, the portable detection system 103 may be calibrated for the power zone. The power zone, also referred as power setting, is a combination of multiple levels of powers corresponding to each calibration value/state. For instance, the power zone to 'P1' may correspond to the calibration value 'PLUSMINUS', the power zone to 'P2' may correspond to the calibration value 'PLUS', and the power zone to 'P0' may correspond to the calibration value 'MINUS'. In the present disclosure where DRS-Linear regression is used to determine specific neurological conditions (i.e., brain condition state of the subject 101) with physiological characteristics, the scalp to cortex distance may vary between subjects (i.e., persons) because of gender, age, skin properties, and the like. The power zone calibration described in this section overcomes the variation in scalp to cortex distance using adaptive technique where reflected signal along with input signal are used as a feedback to select or modify the power zone of the portable detection system 103. The calibrating power zone of the portable detection system 103 may be performed automatically or manually in real-time. The calibrating power zone of the portable detection system 103 may be performed by the calibrating module of the portable detection system 103.

With reference to FIG. 2a, when the portable detection system 103 is switched ON, at step 201, the portable detection system 103 initially sets calibration value to a default calibration value 'PLUSMINUS'. Thereafter, at step 203, the operator of the portable detection system 103 selects a lobe location of the subject 101 on the display screen 131 of the portable detection system 103. The selection of the lobe location may be one of the frontal left lobe $111_1$, frontal right lobe $111_2$, temporal left lobe $113_1$, temporal right lobe $113_2$, parietal left lobe $115_1$, parietal right lobe $115_2$, occipital left lobe $117_1$ and occipital right lobe $117_2$ as shown in FIG. 1b. Once the lobe location is selected for calibration, the portable detection system 103 checks the calibration value at step 205. Since the calibration value is initially set to the default calibration value 'PLUSMINUS', the portable detection system 103 sets power zone to 'P1' at step 209. Based on the power zone to 'P1' which is set, the portable detection system 103 selects or sets input parameters (also, referred to as control variables) such as current and temperature at steps 213, 215, 217. The current limiting module of the portable detection system 103 monitors the set current value at step 219 and stores the set current value in the (internal) memory of the portable detection system 103 at step 221. The stored current value may be used for controlling the scan at step 231 by comparing with set current values in the system at step 227. Similarly, the temperature limiting module of the portable detection system 103 monitors the set temperature value at step 223 and stores the set temperature value in the (internal) memory of the portable detection system 103 at step 225. The stored temperature value may be used for controlling the scan at step 231 by comparing with set temperature values in the system at 227. Thereafter, the portable detection system 103 checks if the set current value is greater than a predefined threshold current value for the power zone 'P1' and if the set temperature value is greater than a predefined threshold temperature value for the power zone 'P1' at step 227. If the above conditions are not satisfied i.e., the set current value is not greater than the predefined threshold current value for the power zone 'P1' or the set temperature value is not greater than the predefined threshold temperature value for the power zone 'P1', the portable detection system 103 induces a temporary or permanent shutdown at step 229. In detail, if the set current value is not greater than the predefined threshold current value for the power zone 'P1', the current limiting module of the portable detection system 103 may induce a temporary or permanent shutdown. If the set temperature value is not greater than the predefined threshold temperature value for the power zone 'P1', the temperature limiting module of the portable detection system 103 may induce a temporary or permanent shutdown. In one embodiment, an interrupt and protection module (not shown in FIG. 2a) may be implemented to temporarily or permanently shutdown the portable detection system 103. However, if the above conditions are satisfied i.e., the set current value is greater than the predefined threshold current value for the power zone 'P1' and the set temperature value is greater than the predefined threshold temperature value for the power zone 'P1', the portable detection system 103 starts scanning selected lob location of the subject 101 at step 231.

For each input signal (also, referred as a transmitted signal or a probe signal) transmitted through the source probe of the portable detection system 103 during scanning, a corresponding reflected signal (also, referred as a detected signal) is received through the detector probe of the portable detection system 103 at step 233. A multiple scanning may be performed for each lobe location of the subject 101. Thereafter, the portable detection system 103 checks the S/N ratio with respect to each of the input signals and corresponding reflected signal at step 235. If the detected signal's S/N ratio is within the predefined threshold S/N range for the power zone 'P1', the portable detection system 103 stores the input and corresponding detected signal value in (internal) memory of the portable detection system 103 at step 241. When the portable detection system 103 reaches the step 241, the portable detection system 103 is said to be calibrated and ready for post-calibration steps described with reference to FIG. 2b.

However, if the S/N ratio check performed at step 235 is not within the predefined threshold S/N range for the power zone 'P1', the portable detection system 103 changes the calibration value from 'PLUSMINUS' to 'PLUS' when the S/N ratio value is not greater than lowest value in the predefined threshold S/N range and changes the calibration value from 'PLUSMINUS' to 'MINUS' when the S/N ratio value is not lower than highest value in the predefined threshold S/N range. Thereafter, the portable detection system 103 repeats the steps from 205 till the portable detection system 103 reaches the step 241 as described above.

In brief, the portable detection system 103 calibrates a power zone of the portable detection system 103 in real-time based on a S/N ratio detected from at least one reflected signal received on scanning a part of the subject's lobe.

With reference to FIG. 2a, three power zones have been implemented for each lobe i.e., the power zone 'P2' when the calibration value is 'PLUS', the power zone 'P1' when the calibration value is 'PLUSMINUS' and the power zone 'P0' when the calibration value is 'MINUS'. In one embodiment, the portable detection system 103 may include, but not limited to, more than three power zones for calibration.

In present disclosure, each calibration value corresponds to a power zone which is a combination of multiple levels of powers generated by varying input parameters (also, referred to as control variables) like current and temperature.

In one embodiment, with reference to FIG. 2a, the step 203 may be performed before the step 201. For instance, when the portable detection system 103 is switched ON, the operator of the portable detection system 103 selects a lobe location of the subject 101 on the display screen 131 of the portable detection system 103. Thereafter, the portable detection system 103 selects or sets calibration value depending on selection of the lobe location of the subject 101. For example, if the lobe location selected is frontal left lobe 111₁, the portable detection system 103 selects or sets calibration value to a default calibration value 'MINUS' and if the lobe location selected is parietal left lobe 115₁, the portable detection system 103 selects or sets calibration value to a default calibration value 'PLUS'. From this point, the portable detection system 103 repeats the steps from 205 till the portable detection system 103 reaches the step 241 as described above. The different default calibration value based on the lobe location of the subject 101 allows considering the anatomical variations between each lobe.

Figure 2B:
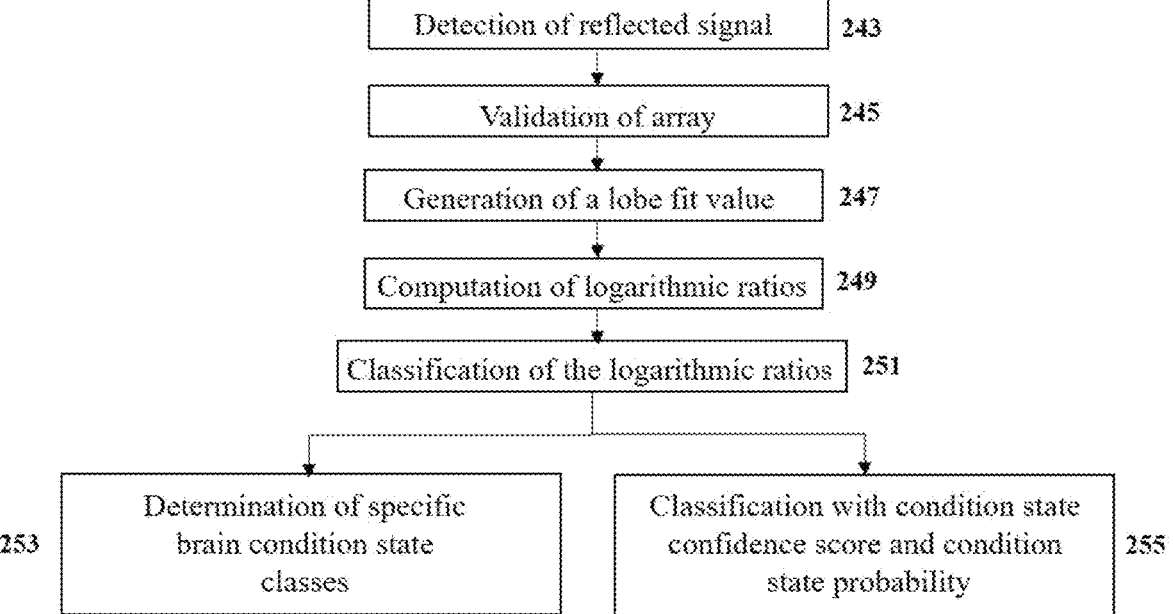
FIG. 2b illustrates a flow chart for detecting brain condition state of a subject post power zone calibration in accordance with some embodiments of the present disclosure.

FIG. 2b illustrates a flow chart for detecting brain condition state of a subject post power zone calibration in accordance with some embodiments of the present disclosure.

Post-calibration of the portable detection system 103, the portable detection system 103 is ready for detecting brain condition state of the subject 101. On scanning each of the lobe locations of the subject 101 after calibration, at step 243 the portable detection system 103 detects a reflected signal through the detector probe for each of a plurality of transmitted input signals through the source probe. For example, for transmitted input signals $X_0$ to $X_N$, corresponding reflected signals $Y_0$ to $Y_N$ are detected. When the scanning is performed, synchronized data acquisition takes place to detect (or capture) the reflected signal. The detected reflected signal is time averaged backscattered signal from underlying tissues at the lobe location of the subject 101. Thereafter, at step 245, the portable detection system 103 validates an array generated using the plurality of transmitted input signal and corresponding reflected signal for each of the lobe locations based on predetermined threshold condition. In detail, the portable detection system 103 generates the array of the plurality of transmitted input signal and corresponding reflected signal for each of the lobe locations. Subsequently, the portable detection system 103 validates the reflected signal in the generated array by determining if each of these values is greater than a minimum predetermined threshold value and less than a maximum predetermined threshold value. When the reflected signal is not greater than the minimum predetermined threshold value or not less than the maximum predetermined threshold value, the portable detection system 103 eliminates at least one transmitted input signal and corresponding reflected signal from the generated array of the plurality of transmitted input signal and corresponding reflected signal. For instance, the portable detection system 103 generates an array i.e., $(X_0, Y_0), (X_1, Y_1) \ldots, (X_N, Y_N)$ from the plurality of transmitted input signal ($X_0$ to $X_N$) and corresponding reflected signal ($Y_0$ to $Y_N$) for each of the lobe locations. The portable detection system 103 determines if:

min_predetermined threshold value $< Y_{0 \ldots N} <$ max_ predetermined threshold value Wherein, min_predetermined threshold value and max_ predetermined threshold value represent acceptable minimum and maximum S/N ratio, respectively.

For example, if Y3 is less than min_predetermined threshold value and Y7 is greater than the max_predetermined threshold value, the portable detection system 103 validates the array by eliminating $(X_3, Y_3)$ and $(X_7, Y_7)$ from the array i.e., $(X_0, Y_0), (X_1, Y_1) \ldots, (X_N, Y_N)$.

In one embodiment, the validated array may be arranged in an ascending order of transmitted input signal values i.e., arranging $(X_0, Y_0), (X_1, Y_1) \ldots, (X_N, Y_N)$ in the ascending values of $X_0, X_1 \ldots, X_N$.

The portable detection system 103 generates a lobe fit value for the validated array for each of the lobe locations using a curve fitting technique at step 247. The curve fitting technique may be, not limiting to, a least square curve fitting technique. The least square curve fitting technique determines the best fit line to data points (i.e., validated array). The slope of best fit line gives lobe fit value (m). For instance, the validated array i.e., $(X_N, Y_N)$ is fed to a curve fitting technique with least square method (shown in equation 1) to generate lobe fit value (m) with minimal residual error.

$$m = \frac{\sum_{i=1}^{n}(x_i - \bar{x})(y_i - \bar{y})}{\sum_{i=1}^{n}(x_i - \bar{x})^2} \tag{1}$$

$$c = \bar{y} - m\bar{x}$$

Wherein, the intercept value 'c' may remain the same for all locations as it corresponds to (photodetection) noise floor when x=0. The $\bar{x}$ and $\bar{y}$ values are average values of $X_0 \ldots X_N$ and $Y_0 \ldots Y_N$, respectively, from the validated array.

At step 249, the portable detection system 103 computes logarithmic ratios corresponding to four pairs of contralateral lobe location, six pairs of ipsilateral lobe locations in left hemisphere (i.e., left half of the part of brain) and six pairs of ipsilateral lobe locations in right hemisphere (i.e., right half of the part of brain) using the lobe fit value generated for the validated array for each of the lobe locations. The four pairs of contralateral lobe location may refer to a (first) pair of frontal left lobe $111_1$ and frontal right lobe $111_2$, a (second) pair of temporal left lobe $113_1$ and temporal right lobe $113_2$, a (third) pair of parietal left lobe $115_1$ and parietal right lobe $115_2$, and a (fourth) pair of occipital left lobe $117_1$ and occipital right lobe $117_2$. The six pairs of ipsilateral lobe locations in left hemisphere may refer to a (first) pair of frontal left lobe $111_1$ and temporal left lobe $113_1$, a (second) pair of frontal left lobe $111_1$ and parietal left lobe $115_1$, a (third) pair of frontal left lobe $111_1$ and occipital left lobe $117_1$, a (fourth) pair of temporal left lobe $113_1$ and parietal left lobe $115_1$, a (fifth) pair of temporal left lobe $113_1$ and occipital left lobe $117_1$, and a (sixth) pair of parietal left lobe $115_1$ and occipital left lobe $117_1$. The six pairs of ipsilateral lobe locations in right hemisphere may refer to a (first) pair of frontal right lobe $111_2$ and temporal right lobe $113_2$, a (second) pair of frontal right lobe $111_2$ and parietal right lobe $115_2$, a (third) pair of frontal right lobe $111_2$ and occipital right lobe $117_2$, a (fourth) pair of temporal right lobe $113_2$ and parietal right lobe $115_2$, a (fifth) pair of temporal right lobe $113_2$ and occipital right lobe $117_2$ and a (sixth) pair of parietal right lobe $115_2$ and occipital right lobe $117_2$. In one embodiment, the logarithmic ratios may be computed or calculated using an enhanced (i.e., further modified) version of Modified Beer-Lambert Law (MBLL) algorithm. The logarithmic ratios are computed using the lobe fit value (m) for each lobe, which is given by equation 2.

$$m_1 = \log_{10}(m_a/m_b) \tag{2}$$

Where, $m_a$ and $m_b$ represent fit values corresponding to any two lobe locations on the subject's head.

At step 251, the portable detection system 103 classifies the logarithmic ratios corresponding to four pairs of contralateral lobe location and six pairs of ipsilateral lobe locations into one of brain condition state classes by comparing with pre-labelled logarithmic ratios stored in the portable detection system 103. The pre-labelled logarithmic ratios may be referred to as historic logarithmic ratios stored in (internal) memory of the portable detection system 103 that is used as a reference to classify the (present) logarithmic ratios. In one embodiment, the brain condition state classes may be binary, comprise of no brain haemorrhage and brain haemorrhage. For instance, the logarithmic ratios may be classified into the brain condition state classes 0 and 1. Here, '0' may indicate no brain haemorrhage and '1' may indicate brain haemorrhage. In another embodiment, the brain condition state classes may comprise of no brain haemorrhage, mild brain haemorrhage, moderate brain haemorrhage, and severe brain haemorrhage. For instance, the logarithmic ratios may be classified into the brain condition state classes 0, 1, 2 and 3. Here, '0' may indicate no brain haemorrhage, '1' may indicate mild brain haemorrhage, '2' may indicate moderate brain haemorrhage, and '3' may indicate severe brain haemorrhage.

In one embodiment, the portable detection system 103 may determine specific brain condition state classes using the logarithmic ratios corresponding to the four pairs of contralateral lobe location, the six pairs of ipsilateral lobe locations in left hemisphere and the six pairs of ipsilateral lobe locations in right hemisphere and Boolean operations at step 253. The specific brain condition state classes may be one of unilateral haemorrhage, bilateral haemorrhage, and both unilateral and bilateral haemorrhage. For instance, the portable detection system 103 may feed the logarithmic ratios to three OR gates for Boolean operations to compute three variables values i.e., 'c', 'il' and 'ir' to detect specific brain condition state classes. The 'c' refers to contralateral logarithmic ratios, 'il' refers to ipsilateral logarithmic ratios for lobe locations in the left hemisphere, and 'ir' refers to ipsilateral logarithmic ratios for lobe locations in the right hemisphere. Once the values of c, il and ir are determined, the portable detection system 103 may determine specific brain condition state classes based on combinations indicated in FIG. 2c.

Figure 2D:
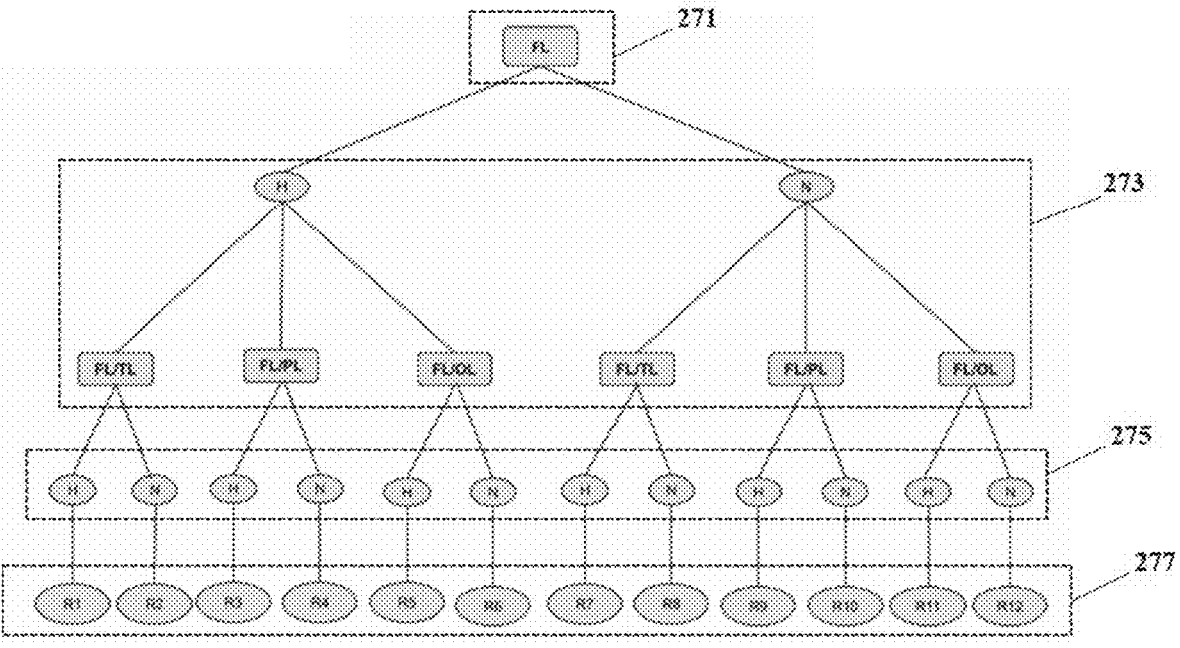
FIG. 2d shows a hierarchical tree-based classification technique in accordance with some embodiments of the present disclosure.

In another embodiment, the portable detection system 103 may classify each of the lobe locations into haemorrhage and not haemorrhage along with condition state confidence score and condition state probability calculated using a classification technique on the logarithmic ratios corresponding to four pairs of contralateral lobe location and six pairs of ipsilateral lobe locations in each hemisphere at step 255. The classification technique may be a hierarchical tree-based classification technique or a machine learning classification technique. For instance, using hierarchical tree-based classification technique, multiple trees may be built such that each lobe location that is scanned has a corresponding tree (referred as lobe location tree), shown in FIG. 2d. Each lobe location tree 271 results in 8 decision nodes 273, 12 leaf nodes 275 and 12 result nodes 277. Each result node terminates in a result for two locations. For example, R1 indicates results for FL and TL. Here, FL refers to frontal lobe, TL refers to temporal lobe, PL refers to parietal lobe and OL refers to occipital lobe. Each result node from R1 and R12 assigns a value 1 or 0 to two locations according to brain haemorrhage or no brain haemorrhage. The confidence score for each lobe location to be brain haemorrhage is computed as the total number of times a result node ends in the particular location being assigned a value 1 (i.e., a brain haemorrhage). Similarly, the confidence score for the same lobe location to be no brain haemorrhage is computed as the total number of times the result nodes end in this location to be assigned a value 0 (i.e., no brain haemorrhage). Hence, for each lobe location (1), there are two confidence scores, confidence score for brain haemorrhage i.e., csh(1) and confidence score for no brain haemorrhage i.e., csn(1).

A location is declared to be brain haemorrhage whenever csh (1)>1. Also, the likelihood is indicated by probability of brain haemorrhage i.e., p(1) computed using equation 3:

$$p(1) = csh(1)/[csh(1) + csn(1)] \tag{3}$$

Instead of hierarchical tree-based classification technique described above, a machine learning classification technique such as K nearest neighbour algorithm, Convolutional Neural Network (CNN), support vector machines and the like may be used to classify each of the lobe locations into haemorrhage and no brain haemorrhage along with condition state confidence score and condition state probability.

Figure 3:
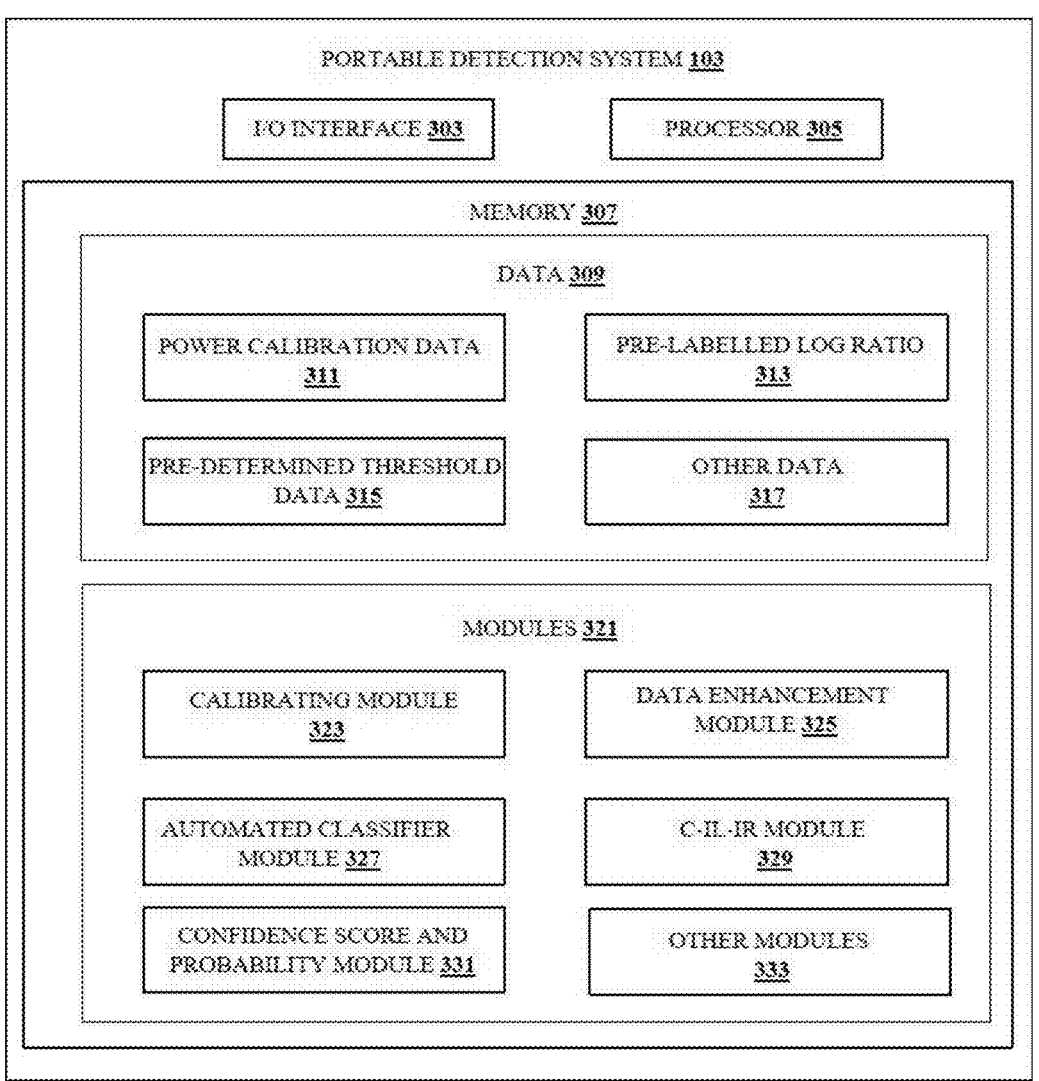
FIG. 3 shows a detailed block diagram of a portable detection system in accordance with some embodiments of the present disclosure.

FIG. 3 shows a detailed block diagram of a portable detection system in accordance with some embodiments of the present disclosure.

In addition to the components such as the source probe, the detector probe, LEDs, buttons, the buzzer and display of the portable detection system 103 described above, the portable detection system 103 may include an I/O interface 303, a processor 305 and a memory 307, as shown in FIG. 3. The source probe and the detector probe of the portable detection system 103 may act as the I/O interface 303. The source probe may transmit an input signal (also, referred to as a transmitted signal or a probe signal) during scanning and the detector probe may receive a corresponding reflected signal (also, referred to as a detected signal).

The input signal transmitted by the I/O interface 303 (i.e., the source probe) and corresponding reflected signal received by the I/O interface 103 (i.e., the detector probe) may be stored in the memory 307. The memory 307 may be communicatively coupled to the processor 305 of the portable detection system 103. The memory 307 may, also, store processor instructions which may cause the processor 305 to execute the instructions for detecting brain condition state of the subject 101.

The processor 305 may include at least one data processor for detecting brain condition state of the subject 101. The processor 305 may include specialized processing units such as integrated system (bus) controllers, memory management control units, floating point units, graphics processing units, digital signal processing units, etc.

The portable detection system 103, in addition to the I/O interface 303 and processor 305 described above, may include data 309 and one or more modules 321, which are described herein in detail. As an example, the data 309 and the modules 321 may be stored within the memory 307 configured in the portable detection system 103. The data 309 may include, for example, power calibration data 311, pre-labelled log ratio 313, predetermined threshold data 315 and other data 317.

The power calibration data 311 may store calibration values and corresponding power zones. For instance, the calibration values 'PLUS', PLUSMINUS' and 'MINUS' and corresponding power zones 'P2', 'P1' and 'P0', respectively, may be stored in the power calibration data 311.

The pre-labelled log ratio 313 may store the pre-labelled logarithmic ratios that is used as a reference to classify the (present) logarithmic ratios. The pre-labelled logarithmic ratios may be referred to as historic logarithmic ratios.

The predetermined threshold data 315 may store minimum predetermined threshold value and maximum predetermined threshold value. These values are used by the portable detection system 103 to determine whether the reflected signal in the generated array is greater than a minimum predetermined threshold value and less than a maximum predetermined threshold value. The min_predetermined threshold value (i.e., minimum predetermined threshold value) and max_predetermined threshold value (i.e., maximum predetermined threshold value) may represent acceptable minimum and maximum S/N ratio, respectively.

The other data 317 may store data, including temporary data and temporary files, generated by one or more modules 321 for performing the various functions of the portable detection system 103.

In some embodiments, the data 309 stored in the memory 307 are processed by the one or more modules 321 of the portable detection system 103. The one or more modules 321 may be stored within the memory 307. As an example, the one or more modules 321 communicatively coupled to the processor 305 configured in the portable detection system 103, may also be present outside the memory 307. In some implementations, the one or more modules 321 may be communicatively coupled to the processor 305 for performing one or more functions of the portable detection system 103. The said modules 321 when configured with the functionality defined in the present disclosure will result in a novel hardware.

In one implementation, the one or more modules 321 may include, but are not limited to, a calibrating module 323, a data enhancement module 325, an automated classifier module 327, a C-IL-IR module 329 and a confidence score and probability module 331. The one or more modules 321 may, also, include other modules 333 to perform various miscellaneous functionalities of the portable detection system 103.

The calibrating module 323 may calibrate a power zone of the portable detection system in real-time based on a S/N ratio detected from at least one reflected signal received on scanning a part of the subject's lobe. The calibrating module 323 may include a current limiting module and a temperature limiting module (not shown in FIG. 3). The calibrating module 323 may perform the power zone calibration as described with reference to the flow chart in FIG. 2a.

The data enhancement module 325 may detect a reflected signal for each of a plurality of transmitted input signals on scanning each of the lobe locations of the subject after calibration. Thereafter, the data enhancement module 325 may validate an array generated using the plurality of transmitted input signal and corresponding reflected signal for each of the lobe locations based on predetermined threshold condition. Subsequently, the data enhancement module 325 may generate a lobe fit value for the validated array for each of the lobe locations using a curve fitting technique. Lastly, the data enhancement module 325 may compute logarithmic ratios corresponding to four pairs of contralateral lobe location, six pairs of ipsilateral lobe locations in left hemisphere and six pairs of ipsilateral lobe locations in right hemisphere using the lobe fit value generated for the validated array for each of the lobe locations.

The automated classifier module 327 may classify the logarithmic ratios corresponding to four pairs of contralateral lobe location and six pairs of ipsilateral lobe locations into one of brain condition state classes by comparing with pre-labelled logarithmic ratios stored in the portable detection system. The automated classifier module 327 may use supervised machine learning technique to classify the logarithmic ratios using the pre-labelled logarithmic ratios stored in the portable detection system.

The C-IL-IR module 329 may determine specific brain condition state classes using the logarithmic ratios corresponding to the four pairs of contralateral lobe location, the six pairs of ipsilateral lobe locations in left hemisphere and the six pairs of ipsilateral lobe locations in right hemisphere and Boolean operations. The specific brain condition state classes may be one of unilateral haemorrhage, bilateral haemorrhage, and both unilateral and bilateral haemorrhage. The C-IL-IR module 329 may comprise three OR gates for Boolean operations to compute three variables values i.e., 'c', 'il' and 'ir' to detect specific brain condition state classes. The 'c' refers to contralateral logarithmic ratios, 'il' refers to ipsilateral logarithmic ratios for lobe locations in the left hemisphere, and 'ir' refers to ipsilateral logarithmic ratios for lobe locations in the right hemisphere. Once the values of c, il and ir are determined, the C-IL-IR module 329 may determine specific brain condition state classes based on combinations indicated in FIG. 2*c*.

The confidence score and probability module 331 may classify each of the lobe locations into haemorrhage and not haemorrhage along with condition state confidence score and condition state probability calculated using a classification technique on the logarithmic ratios corresponding to four pairs of contralateral lobe location and six pairs of ipsilateral lobe locations in each hemisphere. The confidence score and probability module 331 may use a hierarchical tree-based classification technique or a machine learning classification technique.

FIG. 4 illustrates a flowchart showing a method for detecting the brain condition state of a subject in accordance with some embodiments of present disclosure.

As illustrated in FIG. 4, method 400 includes one or more blocks for detecting the brain condition state of a subject. The method 400 may be described in the general context of computer executable instructions. Generally, computer executable instructions can include routines, programs, objects, components, data structures, procedures, modules, and functions, which perform particular functions or implement particular abstract data types.

The order in which the method 400 is described is not intended to be construed as a limitation, and any number of the described method blocks can be combined in any order to implement the method. Additionally, individual blocks may be deleted from the methods without departing from the scope of the subject matter described herein. Furthermore, the method can be implemented in any suitable hardware, software, firmware, or combination thereof.

At block 401, the portable detection system 103 may calibrate a power zone of the portable detection system 103 in real-time based on a Signal-to-Noise (S/N) ratio detected from at least one reflected signal received on scanning a part of the subject's lobe. The calibrating power of the portable detection system 103 may be performed automatically or manually.

At block 403, the portable detection system 103 may detect a reflected signal for each of a plurality of transmitted input signals on scanning each of lobe locations of the subject 101 after calibration. The lobe locations may comprise of frontal left lobe 111₁, frontal right lobe 111₂, temporal left lobe 113₁, temporal right lobe 113₂, parietal left lobe 115₁, parietal right lobe 115₂, occipital left lobe 117₁ and occipital right lobe 117₂.

At block 405, the portable detection system 103 may validate an array generated using the plurality of transmitted input signal and corresponding reflected signal for each of the lobe locations based on predetermined threshold condition. The validating the array generated using the plurality of transmitted input signal and corresponding reflected signal for each of the lobe locations based on predetermined threshold condition may comprise generating the array of the plurality of transmitted input signal and corresponding reflected signal for each of the lobe locations. Thereafter, the validating step may comprise determining whether the reflected signal in the generated array is greater than a minimum predetermined threshold value and less than a maximum predetermined threshold value and eliminating at least one transmitted input signal and corresponding reflected signal from the generated array of the plurality of transmitted input signal and corresponding reflected signal when the reflected signal is not greater than the minimum predetermined threshold value or not less than the maximum predetermined threshold value.

At block 407, the portable detection system 103 may generate a lobe fit value for the validated array for each of the lobe locations using a curve fitting technique. The curve fitting technique may be a least square curve fitting technique.

At block 409, the portable detection system 103 may compute logarithmic ratios corresponding to four pairs of contralateral lobe location, six pairs of ipsilateral lobe locations in left hemisphere and six pairs of ipsilateral lobe locations in right hemisphere using the lobe fit value generated for the validated array for each of the lobe locations.

At block 411, the portable detection system 103 may classify the logarithmic ratios corresponding to four pairs of contralateral lobe location and six pairs of ipsilateral lobe locations into one of brain condition state classes by comparing with pre-labelled logarithmic ratios stored in the portable detection system. The brain condition state classes may be binary consisting of no brain haemorrhage and brain haemorrhage.

Some of the technical advantages of the present disclosure are listed below.

The system disclosed in the present disclosure for detecting brain condition state of a subject is portable, which allows non-invasive onsite detection, easy to use and easy to detect brain condition state. This approach overcomes bulky setup typically used for detecting brain condition state and also, overcomes expensive detection cost by making the detection process very affordable.

The method disclosed in the present disclosure for detecting brain condition state of a subject uses a curve fitting technique, which eliminates outlier effect typically present in results, thereby, improving accuracy for the detection results.

One of the major problems faced in an optical system is that if a low cut-off threshold value is kept for selection of signal value to be used in computation, then accuracy of results is compromised due to noise artefacts. However, if the cut-off threshold value is kept high, then crucial data points are missed, thereby, rendering the optical system less sensitive. The method disclosed in the present disclosure overcomes the above-mentioned problems by allowing the portable detection system to select a lower noise floor value as minimum threshold while maintaining detection accuracy. This is achieved by the combination of a lobe fit value computation, which allows minimum threshold value and the curve fitting technique, which eliminates/minimizes noise effect. This approach makes the portable detection system sensitive to low signal values.

Typically, when a signal is detected, the signal data is required to be normalized before being used for computation. This adds to extra processing steps and processing time. In the present disclosure, the lobe fit values are automatically normalized at the stage of computation of logarithmic ratios. As a result, this approach minimizes the processing step and processing time, making the portable detection system efficient and fast.

One of the common variations that affect the signal consistency in Diffuse Reflectance Spectroscopy (DRS) systems is intersubject variation, which could be anatomical, physiological or demographic and the like. The intersubject variation may arise because of the changes in skin properties owing to age, gender or anatomical differences like scalp to cortex distance. The method disclosed in the present disclosure allows a real time automatic calibration of optical probes of the portable detection system to overcome intersubject variation. The calibrating module of the present disclosure adjusts power zone during calibration based on the intersubject variation and takes corrective actions to reduce or nullify the effect of these variations.

The present disclosure eliminates the need of any human intervention to manually adjust power zones during power zone calibration prior to using the portable detection system for detecting brain condition state of a subject.

The Modified Beer-Lambert Law (MBLL) relates differential changes in the optical density to differential changes in the absorption coefficient. The limitation of the MBLL algorithm is that it will produce accurate output (or result) only if the input value is accurate. As a result, the MBLL algorithm is less accurate when an optical detection system suffers from challenges like changing temperature and changing coupling efficiency between different data acquisition cycles as these variations (or changes) may induce variability in input values acquired at different times. To eliminate the above-mentioned variations, leading to error in the input values, the method disclosed in the present disclosure uses an enhanced (or further modified) version of MBLL algorithm. This approach removes the effect of variations in the input values, thereby, eliminating the selection bias to increase the accuracy of the output values.

One or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, non-volatile memory, hard drives, CD ROMs, DVDs, flash drives, disks, and any other known physical storage media.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may include media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMS, PROMs, RAMs, DRAMs, SRAMs, Flash Memory, firmware, programmable logic, etc.), etc. Further, non-transitory computer-readable media include all computer-readable media except for a transitory. The code implementing the described operations may further be implemented in hardware logic (e.g., an integrated circuit chip, Programmable Gate Array (PGA), Application Specific Integrated Circuit (ASIC), etc.).

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary, a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 4 show certain events occurring in a certain order. In alternative embodiments, certain operations may be performed in a different order, modified, or removed. Moreover, steps may be added to the above-described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that are issued on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

REFERRAL NUMERALS

| Reference number | Description |
| --- | --- |
| 101 | Subject |
| 103 | Portable detection system |
| $111_1$ | Frontal left side lobe location |
| $111_2$ | Frontal right side lobe location |
| $113_1$ | Temporal left side lobe location |
| $113_2$ | Temporal right side lobe location |
| $115_1$ | Parietal left side lobe location |
| $115_2$ | Parietal right side lobe location |

17

-continued

| Reference number | Description |
| --- | --- |
| $117_1$ | Occipital left side lobe location |
| $117_2$ | Occipital right side lobe location |
| 305 | Processor |
| 307 | Memory |
| 309 | Data |
| 311 | Power calibration data |
| 313 | Pre-labelled log ratio |
| 315 | Predetermined threshold data |
| 317 | Other data |
| 321 | Modules |
| 323 | Calibrating module |
| 325 | Data enhancement module |
| 327 | Automated classifier module |
| 329 | C-IL-IR module |
| 331 | Confidence score and probability module |
| 333 | Other modules |

The invention claimed is:

1. A method for detecting brain condition state of a subject, the method comprising:

calibrating, by a portable detection system, a power zone of the portable detection system in real-time based on a Signal-to-Noise (S/N) ratio detected from at least one reflected signal received on scanning a part of the subject's lobe;

detecting, by the portable detection system, a reflected signal for each of a plurality of transmitted input signal, wherein each of the plurality of transmitted input signal is configured to scan each of lobe locations of the subject after calibration;

validating, by the portable detection system, an array generated using the plurality of transmitted input signal and corresponding reflected signal for each of the lobe locations based on predetermined threshold condition;

generating, by the portable detection system, a lobe fit value for the validated array for each of the lobe locations using a curve fitting technique;

computing, by the portable detection system, logarithmic ratios corresponding to four pairs of contralateral lobe location, six pairs of ipsilateral lobe locations in left hemisphere and six pairs of ipsilateral lobe locations in right hemisphere using the lobe fit value generated for the validated array for each of the lobe locations; and classifying, by the portable detection system, the logarithmic ratios corresponding to four pairs of contralateral lobe location and six pairs of ipsilateral lobe locations into one of brain condition state classes by comparing with pre-labelled logarithmic ratios stored in the portable detection system.

2. The method as claimed in claim 1, wherein the lobe locations comprise of frontal left lobe, frontal right lobe, temporal left lobe, temporal right lobe, parietal left lobe, parietal right lobe, occipital left lobe and occipital right lobe.

3. The method as claimed in claim 1, wherein the calibrating power zone of the portable detection system is performed automatically or manually.

4. The method as claimed in claim 1, wherein the validating the array generated using the plurality of transmitted input signal and corresponding reflected signal for each of the lobe locations based on predetermined threshold condition comprises:

generating, by the portable detection system, the array of the plurality of transmitted input signal and corresponding reflected signal for each of the lobe locations;

determining, by the portable detection system, whether the reflected signal in the generated array is greater than a minimum predetermined threshold value and less than a maximum predetermined threshold value; and eliminating, by the portable detection system, at least one transmitted input signal and corresponding reflected signal from the generated array of the plurality of transmitted input signal and corresponding reflected signal when the reflected signal is not greater than the minimum predetermined threshold value or not less than the maximum predetermined threshold value.

5. The method as claimed in claim 1, wherein the brain condition state classes comprise no brain hemorrhage and brain hemorrhage.

6. The method as claimed in claim 1, wherein the brain condition state classes comprise no brain hemorrhage, mild brain hemorrhage, moderate brain hemorrhage, and severe brain hemorrhage.

7. The method as claimed in claim 1, further comprising:

determining, by the portable detection system, specific brain condition state classes using the logarithmic ratios corresponding to the four pairs of contralateral lobe location, the six pairs of ipsilateral lobe locations in left hemisphere and the six pairs of ipsilateral lobe locations in right hemisphere and Boolean operations, wherein the specific brain condition state classes is one of unilateral hemorrhage, bilateral hemorrhage, and both unilateral and bilateral hemorrhage.

8. The method as claimed in claim 1, further comprising:

classifying, by the portable detection system, each of the lobe locations into hemorrhage and not hemorrhage along with condition state confidence score and condition state probability calculated using a classification technique on the logarithmic ratios corresponding to four pairs of contralateral lobe location and six pairs of ipsilateral lobe locations in each hemisphere, wherein the classification technique is a hierarchical tree-based classification technique or a machine learning classification technique.

9. The method as claimed in claim 1, wherein the curve fitting technique is of a least square curve fitting technique.

10. A portable detection system for detecting brain condition state of a subject, the portable detection system comprising:

a processor; and a memory communicatively coupled to the processor, wherein the memory stores processor-executable instructions, which on execution, cause the processor to calibrate a power zone of the portable detection system in real-time based on a Signal-to-Noise (S/N) ratio detected from at least one reflected signal received on scanning a part of the subject's lobe;

detect a reflected signal for each of a plurality of transmitted input signal, wherein each of the plurality of transmitted input signal is configured to scan each of lobe locations of the subject after calibration;

validate an array generated using the plurality of transmitted input signal and corresponding reflected signal for each of the lobe locations based on predetermined threshold condition;

generate a lobe fit value for the validated array for each of the lobe locations using a curve fitting technique;

compute logarithmic ratios corresponding to four pairs of contralateral lobe location, six pairs of ipsilateral lobe locations in left hemisphere and six pairs of ipsilateral lobe locations in right hemisphere using the lobe fit value generated for the validated array for each of the lobe locations; and classify the logarithmic ratios corresponding to four pairs of contralateral lobe location and six pairs of ipsilateral lobe locations into one of brain condition state classes by comparing with pre-labelled logarithmic ratios stored in the portable detection system.

11. The portable detection system as claimed in claim 10, wherein the lobe locations comprise of frontal left lobe, frontal right lobe, temporal left lobe, temporal right lobe, parietal left lobe, parietal right lobe, occipital left lobe and occipital right lobe.

12. The portable detection system as claimed in claim 10, wherein the curve fitting technique is of a least square curve fitting technique.

13. The portable detection system as claimed in claim 10 is configured to:

generate the array of the plurality of transmitted input signal and corresponding reflected signal for each of the lobe locations;

determine whether the reflected signal in the generated array is greater than a minimum predetermined threshold value and less than a maximum predetermined threshold value; and eliminate at least one transmitted input signal and corresponding reflected signal from the generated array of the plurality of transmitted input signal and corresponding reflected signal when the reflected signal is not greater than the minimum predetermined threshold value or not less than the maximum predetermined threshold value.

14. The portable detection system as claimed in claim 10, wherein the brain condition state classes comprises no brain hemorrhage and brain hemorrhage.

15. The method as claimed in claim 10, wherein the brain condition state classes comprise no brain hemorrhage, mild brain hemorrhage, moderate brain hemorrhage, and severe brain hemorrhage.

16. The portable detection system as claimed in claim 10 is configured to:

determine specific brain condition state classes using the logarithmic ratios corresponding to the four pairs of contralateral lobe location, the six pairs of ipsilateral lobe locations in left hemisphere and the six pairs of ipsilateral lobe locations in right hemisphere and Boolean operations, wherein the specific brain condition state classes is one of unilateral hemorrhage, bilateral hemorrhage, and both unilateral and bilateral hemorrhage.

17. The portable detection system as claimed in claim 10 is configured to:

classify each of the lobe locations into hemorrhage and not hemorrhage along with condition state confidence score and condition state probability calculated using a classification technique on the logarithmic ratios corresponding to four pairs of contralateral lobe location and six pairs of ipsilateral lobe locations in each hemisphere, wherein the classification technique is a hierarchical tree-based classification technique or a machine learning classification technique.

* * * * *